US010765380B2

(12) United States Patent
Everman et al.

(10) Patent No.: US 10,765,380 B2
(45) Date of Patent: Sep. 8, 2020

(54) SYSTEMS AND METHODS FOR MEASURING PHYSIOLOGICAL PARAMETERS

(71) Applicants: Bradford R Everman, Haddonfield, NJ (US); Brian Scott Bradke, Brookfield, VT (US)

(72) Inventors: Bradford R Everman, Haddonfield, NJ (US); Brian Scott Bradke, Brookfield, VT (US)

( * ) Notice: Subject to any disclaimer, the term of this patent is extended or adjusted under 35 U.S.C. 154(b) by 0 days.

(21) Appl. No.: 16/012,713

(22) Filed: Jun. 19, 2018

(65) Prior Publication Data

US 2018/0310893 A1 Nov. 1, 2018

Related U.S. Application Data

(63) Continuation-in-part of application No. 15/492,612, filed on Apr. 20, 2017.

(51) Int. Cl.
| | | |
|---|---|---|
| *A61B 5/00* | (2006.01) | |
| *A61B 5/0205* | (2006.01) | |
| *A61B 5/1455* | (2006.01) | |
| *A61B 5/0482* | (2006.01) | |
| *A61B 5/04* | (2006.01) | |
| *A61B 5/16* | (2006.01) | |
| *A61B 5/024* | (2006.01) | |
| *A61B 5/021* | (2006.01) | |
| *A61B 5/0295* | (2006.01) | |

(52) U.S. Cl.
CPC ............ *A61B 5/746* (2013.01); *A61B 5/0205* (2013.01); *A61B 5/04008* (2013.01); *A61B 5/0482* (2013.01); *A61B 5/14552* (2013.01); *A61B 5/14553* (2013.01); *A61B 5/165* (2013.01); *A61B 5/6803* (2013.01); *A61B 5/6814* (2013.01); *A61B 5/7405* (2013.01); *A61B 5/0075* (2013.01); *A61B 5/021* (2013.01); *A61B 5/0295* (2013.01); *A61B 5/02433* (2013.01); *A61B 5/4809* (2013.01); *A61B 5/742* (2013.01); *A61B 5/7455* (2013.01)

(58) Field of Classification Search
CPC combination set(s) only.
See application file for complete search history.

(56) References Cited

U.S. PATENT DOCUMENTS

| 4,072,831 A | * | 2/1978 | Joscelyn | ................ | H04R 1/083 |
| | | | | | 381/344 |
| H1039 H | * | 4/1992 | Tripp, Jr. | ................. | 128/201.23 |

(Continued)

*Primary Examiner* — Michael W Kahelin
*Assistant Examiner* — Shirley X Jian
(74) *Attorney, Agent, or Firm* — Caldwell Intellectual Propert

(57) ABSTRACT

A system for measuring physiological parameters includes a housing mounted to an exterior body surface of a user. The system includes at least a sensor attached to the housing and contacting the exterior body surface at a locus on a head of the user, the at least a sensor configured to detect at least a physiological parameter and transmit an electrical signal as a result of the detection. The system includes an alert circuit communicatively coupled to the at least sensor, the alert circuit configured to receive at least a signal from the at least a sensor, generate an alarm as a function of the at least a signal, and to transmit the alarm to a user-signaling device communicatively coupled to the alert circuit.

29 Claims, 7 Drawing Sheets

(56) References Cited

U.S. PATENT DOCUMENTS

| | | | | |
|---|---|---|---|---|
| 5,372,134 | A * | 12/1994 | Richardson | A61B 5/02422 600/323 |
| 6,078,829 | A * | 6/2000 | Uchida | A61B 5/6817 600/310 |
| 6,102,856 | A * | 8/2000 | Groff | A61B 5/02055 128/903 |
| 6,198,394 | B1 * | 3/2001 | Jacobsen | A61B 5/1112 340/10.1 |
| 6,527,711 | B1 * | 3/2003 | Stivoric | A61B 5/0002 128/898 |
| 6,610,012 | B2 * | 8/2003 | Mault | A61B 5/0011 600/300 |
| 7,488,294 | B2 * | 2/2009 | Torch | A61B 3/0066 600/372 |
| 8,725,311 | B1 * | 5/2014 | Breed | G08B 21/06 600/300 |
| 9,102,417 | B1 * | 8/2015 | Young | A61B 5/18 |
| 9,826,941 | B1 * | 11/2017 | Serovy | A61B 5/746 |
| 9,853,672 | B2 * | 12/2017 | Ko | H04B 1/385 |
| 10,328,852 | B2 * | 6/2019 | Wilson | B60Q 9/00 |
| 10,419,053 | B2 * | 9/2019 | Ruttler | H04W 76/14 |
| 2002/0148470 | A1 * | 10/2002 | Blue | A61M 16/0677 128/204.22 |
| 2004/0206353 | A1 * | 10/2004 | Conroy, Jr. | A61B 5/14551 128/204.23 |
| 2007/0273611 | A1 * | 11/2007 | Torch | A61B 3/0066 345/8 |
| 2008/0161673 | A1 * | 7/2008 | Goodall | A61B 5/04001 600/409 |
| 2009/0018419 | A1 * | 1/2009 | Torch | A61B 3/0066 600/318 |
| 2009/0058660 | A1 * | 3/2009 | Torch | A61B 3/0066 340/573.1 |
| 2011/0015503 | A1 * | 1/2011 | Joffe | A61B 5/04004 600/301 |
| 2012/0197092 | A1 * | 8/2012 | Luo | A61B 5/0478 600/301 |
| 2013/0109997 | A1 * | 5/2013 | Linke | G06F 19/3418 600/549 |
| 2013/0174845 | A1 * | 7/2013 | Vinnakota | A62B 9/006 128/204.22 |
| 2013/0278631 | A1 * | 10/2013 | Border | G02B 27/017 345/633 |
| 2013/0338446 | A1 * | 12/2013 | Van Vugt | A61B 5/6803 600/300 |
| 2014/0123980 | A1 * | 5/2014 | Rissacher | A61B 5/6803 128/204.23 |
| 2015/0102925 | A1 * | 4/2015 | Foldyna | G16H 50/20 340/539.12 |
| 2015/0280763 | A1 * | 10/2015 | Ko | H04B 1/385 455/73 |
| 2015/0342542 | A1 * | 12/2015 | An | A61B 5/747 455/404.2 |
| 2016/0332567 | A1 * | 11/2016 | Wilson | B60Q 9/00 |
| 2017/0258329 | A1 * | 9/2017 | Marsh | G01J 5/0215 |
| 2019/0212198 | A1 * | 7/2019 | Marsh | A61B 5/01 |

* cited by examiner

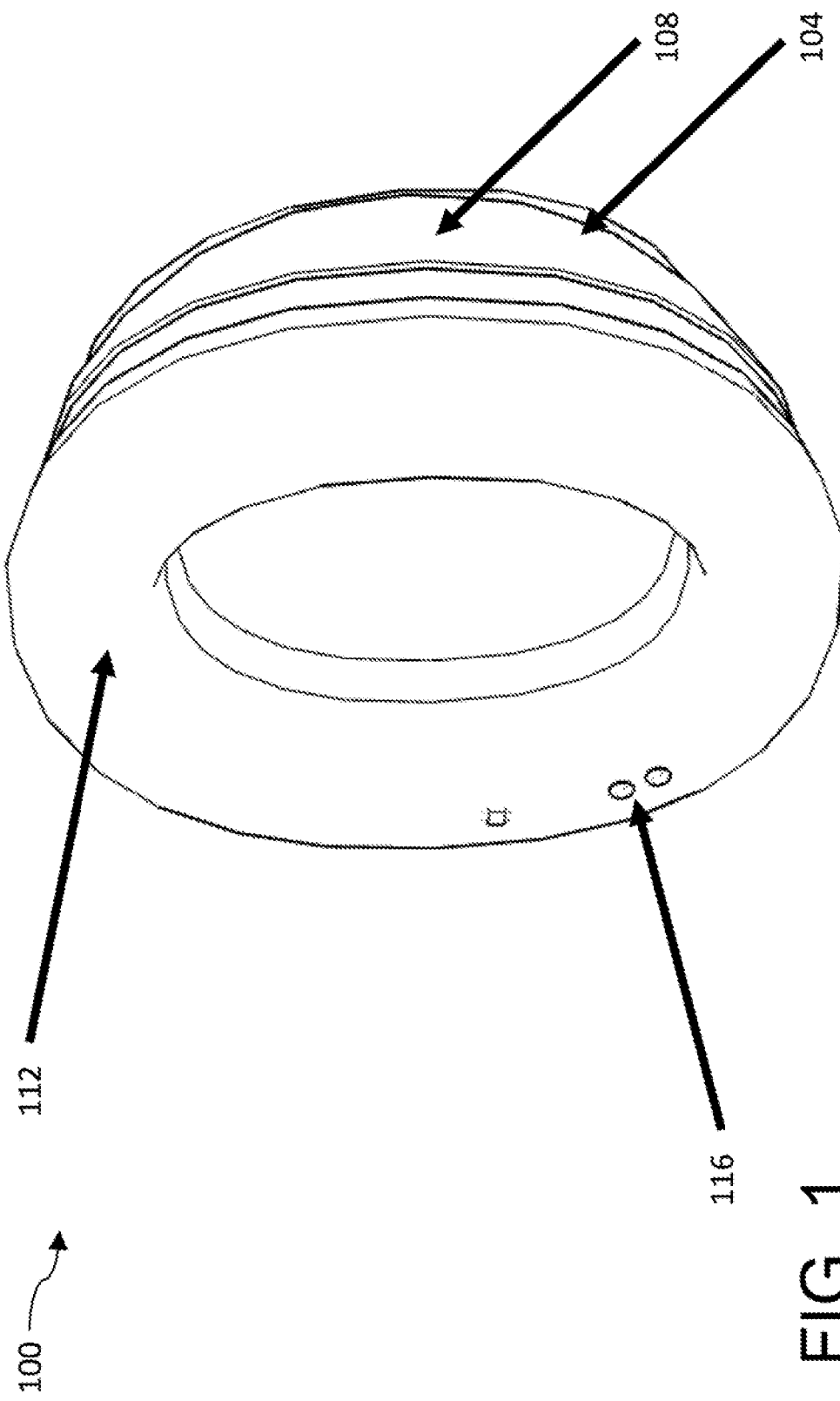

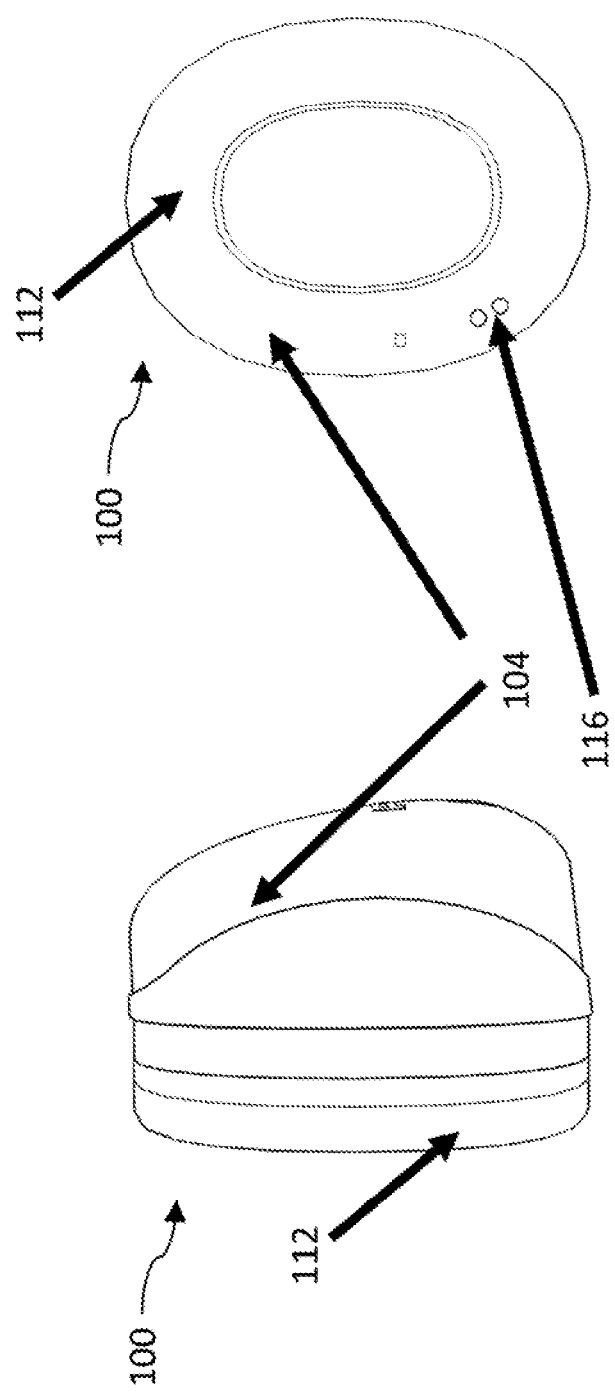

SYSTEMS AND METHODS FOR MEASURING PHYSIOLOGICAL PARAMETERS

RELATED APPLICATION DATA

This application is a continuation in part of U.S. nonprovisional patent application Ser. No. 15/492,612, filed on Apr. 20, 2017, and titled "HUMAN PERFORMANCE OXYGEN SENSOR," the entirety of which is incorporated herein by reference.

FIELD OF THE INVENTION

This invention relates to physiological sensing devices, and in particular to systems and methods for measuring physiological parameters.

BACKGROUND

Blood oxygen saturation can determine a plurality of physical characteristics and ailments, including determining whether an individual is on the verge of losing consciousness. Typically, sensors measuring oxygenation are placed on the fingers or foreheads of patients and do not include a means of analyzing the data and alerting the user or a third party of whether an issue has been determined.

SUMMARY OF THE DISCLOSURE

According to an aspect, a system for measuring physiological parameters includes a housing mounted to an exterior body surface of a user. The system includes at least a sensor attached to the housing and contacting the exterior body surface at a locus on a head of the user, the at least a sensor configured to detect at least a physiological parameter and transmit an electrical signal as a result of the detection. The system includes an alert circuit communicatively coupled to the at least sensor, the alert circuit configured to receive at least a signal from the at least a sensor, generate an alarm as a function of the at least a signal, and to transmit the alarm to a user-signaling device communicatively coupled to the alert circuit.

According to another aspect, a method of measuring at least a physiological parameter includes positioning a physiological parameter measuring device comprising a housing, at least a sensor, and an alert circuit communicatively coupled to the at least a sensor on a user. Positioning further includes mounting the housing on an exterior body surface of the user and placing the at least a sensor in contact with the exterior body surface. The method includes measuring, by the alert circuit and using the at least a sensor, at least a physiological parameter. The method includes detecting, by the alert circuit, a physiological alarm condition, as a function of the at least a physiological parameter. The method includes generating, by the alert circuit, at least an alarm as a function of the detected physiological alarm condition.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 1 shows a perspective view of a device according to an embodiment of the present invention;

FIG. 2 shows a front view of a device according to an embodiment of the present invention;

FIG. 3 shows a side view of a device according to an embodiment of the present invention;

DETAILED DESCRIPTION

Figure 4:
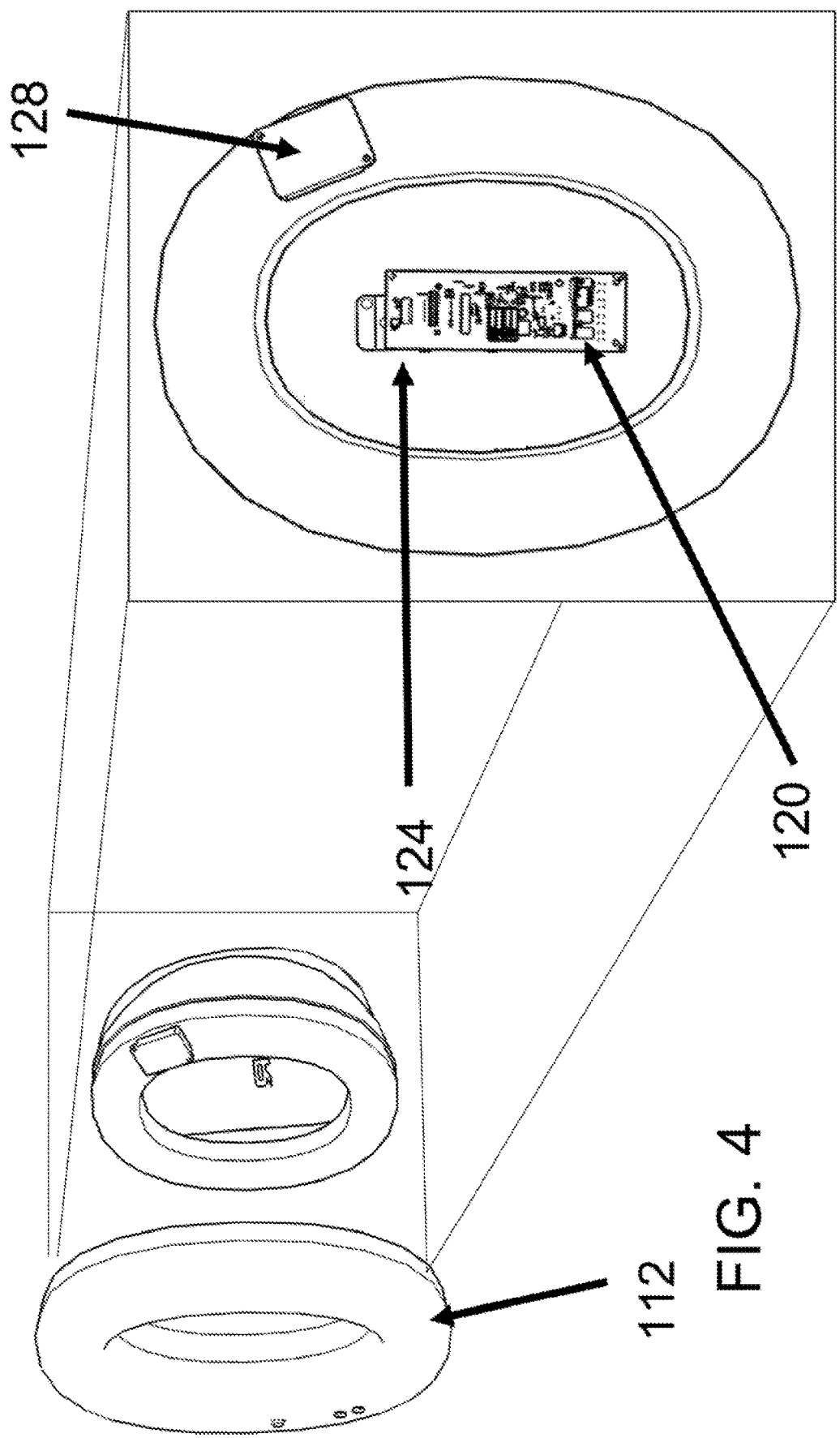
FIG. 4 shows a perspective view of a device according to an embodiment of the present invention.

In an embodiment, devices and methods disclosed herein enable a system to detect physiological parameters such as blood oxygen level, blood pressure, and heart rate of a user through nonintrusive means. Sensors mounted in optimal locations on the head or neck of the user may detect physiological parameters accurately, minimizing interference in activities the user engages in while obtaining a clearer signal than otherwise would be possible. Embodiments of the disclosed device may provide users such as pilots, firemen, and divers who are operating under extreme circumstances with an early warning regarding potential crises such as loss of consciousness, affording the user a few precious extra seconds to avert disaster. Alarms may be provided to the user via bone-conducting transducers or by integration into displays the user is operating, increasing the likelihood that the user will notice the warning in time.

Referring now to FIGS. 1-5, an exemplary embodiment of a perspective view (FIG. 1), a side view (FIG. 2), a front view (FIG. 3), a perspective view (FIG. 4), and a front sectional view (FIG. 5) of a device for measuring physiological parameters 100 is illustrated. Referring now to FIG. 1, device for measuring physiological parameters 100 includes a housing 104. Housing 104 may be mounted to an exterior body surface of a user; exterior body surface may include, without limitation, skin, nails such as fingernails or toenails, hair, an interior surface of an orifice such as the mouth, nose, or ears, or the like. A locus on exterior body surface for mounting of housing 104 and/or other components of device may be selected for particular purposes as described in further detail below. Exterior body surface and/or locus may include an exterior body surface of user's head, face, or neck. Housing 104 may be constructed of any material or combination of materials, including without limitation metals, polymer materials such as plastics, wood, fiberglass, carbon fiber, or the like. Housing 104 may include a substantially rigid outer shell 108. Substantially rigid outer shell 108 may, for instance, protect elements of device 100 from damage, and maintain them in a correct position on a user's body as described in further detail below. Housing 104 and/or substantially rigid outer shell 108 may be inserted between a helmet worn on a head of the user and the exterior body surface; housing 104 and/or substantially rigid outer shell 108 may be shaped to fit between the helmet and the exterior body surface. As a non-limiting example, exterior body surface may be a surface, such as a surface of the head, face, or neck of user, which is wholly or partially covered by helmet, as described for example in further detail below. As a further non-limiting example, housing 104 may be formed to have a similar or identical shape to a standard-issue "ear cup" incorporated in an aviation helmet, so that housing 104 can replace ear cup after ear cup has been removed.

Still viewing FIGS. 1-5, housing 104 may include a seal 112 that rests against exterior body surface when housing 104 is mounted thereon. Seal 112 may be substantially pliable; seal 112 may be constructed of elastomeric, elastic, or flexible materials including without limitation flexible, elastomeric, or elastic rubber, plastic, silicone including medical grade silicone, gel, and the like. Substantially pliable seal 112 may include any combination of materials demonstrating flexible, elastomeric, or elastic properties, including without limitation foams covered with flexible membranes or sheets of polymer, leather, or textile material. As a non-limiting example, substantially pliable seal 112 may include any suitable pliable material for placement over a user's ear, including without limitation any pliable material or combination of materials suitable for use on headphones, headsets, earbuds, or the like. In an embodiment, substantially pliable seal 112 advantageously aids in maintaining housing 104 and/or other components of device 100 against exterior body surface; for instance, where exterior body surface has elastomeric properties and may be expected to flex, stretch, or otherwise alter its shape or position to during operation, substantially pliable seal 112 may also stretch, flex, or otherwise alter its shape similarly under similar conditions, which may have the effect of maintaining seal 112 and/or one or more components of device 100 as described in greater detail below, in consistent contact with the exterior body surface. Seal 112 may be attached to housing 104 by any suitable means, including without limitation adhesion, fastening by stitching, stapling, or other penetrative means, snapping together or otherwise engaging interlocking parts, or the like. Seal 112 may be removably attached to housing 104, where removable attachment signifies attachment according to a process that permits repeated attachment and detachment without noticeable damage to housing 104 and/or seal 112, and without noticeable impairment of an ability to reattach again by the same process. As a non-limiting example, substantially pliable seal 112 may be placed on an ear cup (for instance shown for exemplary purposes in FIG. 3) of the housing 104.

With continued reference to FIGS. 1-5, housing 104 may include, be incorporated in, or be attached to an element containing additional components to device 100. For instance, in an embodiment, housing 104 may include, be incorporated in, or be attached to a headset; headset may include, without limitation, an aviation headset, such as headsets as manufactured by the David Clark company of Worcester Mass., or similar apparatuses. In some embodiments, housing 104 is headset; that is, device 100 may be manufactured by incorporating one or more components into the headset, using the headset as a housing 104. As a further non-limiting example, housing 104 may include a mask; a mask as used herein may include any device or element of clothing that is worn on a face of user during operation, occluding at least a part of the face. Masks may include, without limitation, safety googles, gas masks, dust masks, self-contained breathing apparatuses (SCBA), self-contained underwater breathing apparatuses (SCUBA), and/or other devices worn on and at least partially occluding the face for safety, functional, or aesthetic purposes. Housing 104 may be mask; that is, device 100 may be manufactured by incorporating one or more elements or components of device 100 in or on mask, using mask as housing 104. Housing 104 may include, be incorporated in, or be attached to an element of headgear, defined as any element worn on and partially occluding a head or cranium of user. Headgear may wholly or partially occlude user's face and thus also include a mask; headgear may include, for instance, a fully enclosed diving helmet, space helmet or helmet incorporated in a space suit, or the like. Headgear may include a headband, such as without limitation a headband of a headset, which may be an aviation headset. Headgear may include a hat. Headgear may include a helmet, including a motorcycle helmet, a helmet used in automobile racing, any helmet used in any military process or operation, a construction "hard-hat," a bicycle helmet, or the like. In an embodiment, housing 104 is shaped to conform to a particular portion of user anatomy when placed on exterior body surface; when placed to so conform, housing 104 may position at least a sensor and/or user signaling device in a locus chosen as described in further detail below. For instance, where housing 104 is incorporated in a helmet, mask, earcup or headset, housing 104 may be positioned at a particular portion of user's head when helmet, mask, earcup or headset is worn, which may in turn position at least a sensor and/or user signaling device at a particular locus on user's head or neck.

Continuing to refer to FIGS. 1-5, device 100 includes at least a sensor 116. At least a sensor 116 is configured to detect at least a physiological parameter and transmit an electrical signal as a result of the detection; transmission of an electrical signal, as used herein, includes any detectable alternation of an electrical parameter of an electrical circuit incorporating at least a sensor 116. For instance, at least a sensor 116 may increase or reduce the impedance and/or resistance of a circuit to which at least a sensor 116 is connected. At least a sensor 116 may alter a voltage or current level, frequency, waveform, amplitude, or other characteristic at a locus in circuit. Transmission of an electrical signal may include modulation or alteration of power circulating in circuit; for instance transmission may include closing a circuit, transmitting a voltage pulse through circuit, or the like. Transmission may include driving a non-electric signaling apparatus such as a device for transmitting a signal using magnetic or electric fields, electromagnetic radiation, optical or infrared signals, or the like.

Still referring to FIGS. 1-5, detection of at least a physiological parameter, as used herein, includes detection of any datum describing a physiological state of user. At least a physiological parameter may include at least a circulatory parameter, which may include any detectable parameter describing the state of blood vessels such as arteries, veins, or capillaries, any datum describing the rate, volume, pressure, pulse rate, or other state of flow of blood or other fluid through such blood vessels, chemical state of such blood or other fluid, or any other parameter relative to health or current physiological state of user as it pertains to the cardiovascular system. As a non-limiting example, at least a circulatory parameter may include a blood oxygenation level of user's blood. At least a circulatory parameter may include a pulse rate. At least a circulatory parameter may include a blood pressure level. At least a circulatory parameter may include heart rate variability and rhythm. At least a circulatory parameter may include a plethysmograph describing user blood-flow; in an embodiment, plethysmograph may describe a reflectance of red or near-infrared light from blood. One circulatory parameter may be used to determine, detect, or generate another circulatory parameter; for instance, a plethysmograph may be used to determine pulse oxygen level (for instance by detecting plethysmograph amplitude), pulse rate (for instance by detecting plethysmograph frequency), heart rate variability and rhythm (for instance by tracking pulse rate and other factors over time), and blood pressure, among other things.

With continued reference to FIGS. 1-5, at least a physiological parameter may include neural oscillations generated by user neurons, including without limitation neural oscillations detected in the user's cranial region, sometimes referred to as "brainwaves." Neural oscillations include electrical or magnetic oscillations generated by neurological activity, generally of a plurality of neurons, including superficial cranial neurons, thalamic pacemaker cells, or the like. Neural oscillations may include alpha waves or Berger's waves, characterized by frequencies on the order of 7.5-12.5 Hertz, beta waves, characterized by frequencies on the order of 13-30 Hertz, delta waves, having frequencies ranging from 1-4 Hertz, theta waves, having frequencies ranging from 4-8 Hertz, low gamma waves having frequencies from 30-70 Hertz, and high gamma waves, which have frequencies from 70-150 Hertz. Neurological oscillations may be associated with degrees of wakefulness, consciousness, or other neurological states of user, for instance as described in further detail below. At least a sensor may detect body temperature of at least a portion of user's body, using any suitable method or component for temperature sensing.

Still referring to FIGS. 1-5, at least a sensor 116 may include an optical sensor, which detects light emitted, reflected, or passing through human tissue. Optical sensor may include a near-infrared spectroscopy sensor (NIRS). A NIRS, as used herein, is a sensor that detects signals in the near-infrared electromagnetic spectrum region, having wavelengths between 780 nanometers and 2,500 nanometers. FIG. 6 illustrates an exemplary embodiment of a NIRS 600 against an exterior body surface, which may include skin. NIRS 600 may include a light source 604, which may include one or more light-emitting diodes (LEDs) or similar element. Light source 604 may, as a non-limiting example, convert electric energy into near-infrared electromagnetic signals. Light source 604 may include one or more lasers. NIRS 600 may include one or more detectors 608 configured to detect light in the near-infrared spectrum. Although the wavelengths described herein are infrared and near-infrared, light source 604 may alternatively or additionally emit light in one or more other wavelengths, including without limitation blue, green, ultraviolet, or other light, which may be used to sense additional physiological parameters. In an embodiment, light source may include one or more multi-wavelength light emitters, such as one or more multi-wavelength LEDs, permitting detection of blood-gas toxicology. Additional gases or other blood parameters so detected may include, without limitation $CO_2$ saturation levels, state of hemoglobin as opposed to blood oxygen saturation generally. One or more detectors 608 may include, without limitation, charge-coupled devices (CCDs) biased for photon detection, indium gallium arsenide (InGaAs) photodetectors, lead sulfide (PbS) photodetectors, or the like. NIRS 600 may further include one or more intermediary optical elements (not shown), which may include dispersive elements such as prisms or diffraction gratings, or the like. In an embodiment, NIRS 600 may be used to detect one or more circulatory parameters, which may include any detectable parameter further comprises at least a circulatory parameter. At least a sensor 116 may include at least two sensors mounted on opposite sides of user's cranium.

Referring again to FIGS. 1-5, at least a sensor 116 may include a neural activity sensor. A neural activity sensor, as used herein, includes any sensor disposed to detect electrical or magnetic phenomena generated by neurons, including cranial neurons such as those located in the brain or brainstem. Neural activity sensor may include an electroencephalographic sensor. Neural activity sensor may include a magnetoencephalographic sensor. In an embodiment, neural activity sensor may be configured to detect neural oscillations. At least a sensor may include an eye-tracking sensor, such as one or more cameras for tracking the eyes of user. Eye-tracking sensor may include, as a non-limiting example, one or more electromyographic (EMG) sensors, which may detect electrical activity of eye muscles; electrical activity may indicate activation of one or more eye muscles to move the eye, and used by a circuit such s an alert circuit as described below to determine a movement of user's eyeball, and thus its current location of focus.

Still viewing FIGS. 1-5, at least a sensor 116 may be attached to housing 104; attachment to housing 104 may include mounting on an exterior surface of housing 104, incorporation within housing 104, electrical connection to another element within housing 104, or the like. Alternatively or additionally, at least a sensor 116 may include a sensor that is not attached to housing 104, or is indirectly attached via wiring or the like. As a non-limiting example, at least a sensor 116 and/or one or more components thereof may be coupled to the substantially pliable seal 112. In an embodiment, at least a sensor 116 may be contacting exterior body surface; this may include direct contact with the exterior body surface, or indirect contact for instance through a portion of seal 112 or other components of device 100. In an embodiment, at least a sensor 116 may contact a locus on the exterior body surface where substantially no muscle is located between the exterior body surface and an underlying bone structure, meaning muscle is not located between the exterior body surface and an underlying bone structure and/or any muscle tissue located there is unnoticeable to a user as a muscle and/or incapable of appreciably flexing or changing its width in response to neural signals; such a locus may include, as a non-limiting example, locations on the upper cranium, forehead, nose, behind the ear, at the end of an elbow, on a kneecap, at the coccyx, or the like. Location at a locus where muscle is not located between exterior body surface and underlying bone structure may decrease reading interference and/or inaccuracies created by movement and flexing of muscular tissue. At least a sensor 116 may contact a locus having little or no hair on top of skin. At least a sensor 116 may contact a locus near to a blood vessel, such as a locus where a large artery such as the carotid artery or a branch thereof, or a large vein such as the jugular vein, runs near to skin or bone at the location; in an embodiment, such a position may permit at least a sensor 116 to detect circulatory parameters as described above.

As a non-limiting example of placement of at least a sensor 116, and as illustrated for exemplary purposes in FIGS. 1-5, at least a sensor 116 may include a sensor mounted on an edge of an earcup, and so positioned that placement of earcup over user's ear places sensor in contact with user's head just behind the ear at a local skeletal eminence, with substantially no muscle tissue between skin and bone and a branch of the carotid artery nearby for detection of circulatory parameters. Similarly, where housing 104 includes a mask as described above, a sensor of at least a sensor 116 may be disposed within mask at a location that, when mask is worn, places sensor against a forehead of user.

Still viewing FIGS. 1-5, where at least a sensor 116 includes a neural activity sensor, at least a sensor 116 may include one or more sensors placed in locations suitable for detection of neural activity, such as on upper surfaces of a cranium of user, or similar locations as suitable for EEG or MEG detection and measurement.

With continued reference to FIGS. 1-5, device 100 includes an alert circuit 120 communicatively coupled to the at least sensor. As used herein, "communicative coupling" is a process whereby one device, component, or circuit is able to receive data from and/or transmit data to another device, component, or circuit. In an embodiment, communicative coupling includes electrically coupling at least an output of one device, component, or circuit to at least an input of another device, component, or circuit. Communicative coupling may further be performed by creating an optical, inductive, or other coupling between two or more devices. Communicative coupling may include placing two or more devices in near field communication with one another. Communicative coupling may include configuring two or more devices to send and/or receive signals to or from each other. Communicative coupling may include direct or indirect coupling; for instance, two or more devices may be connected or otherwise communicatively coupled by way of an intermediate circuit. Communicative coupling may be performed via a bus or other facility for intercommunication between elements of a computing device as described in further detail below in reference to FIG. 8. Communicative coupling may include fabrication together on a shared integrated circuit and/or wafer; for instance, and without limitation, two or more communicatively coupled devices may be combined in a single monolithic unit or module.

Figure 5:
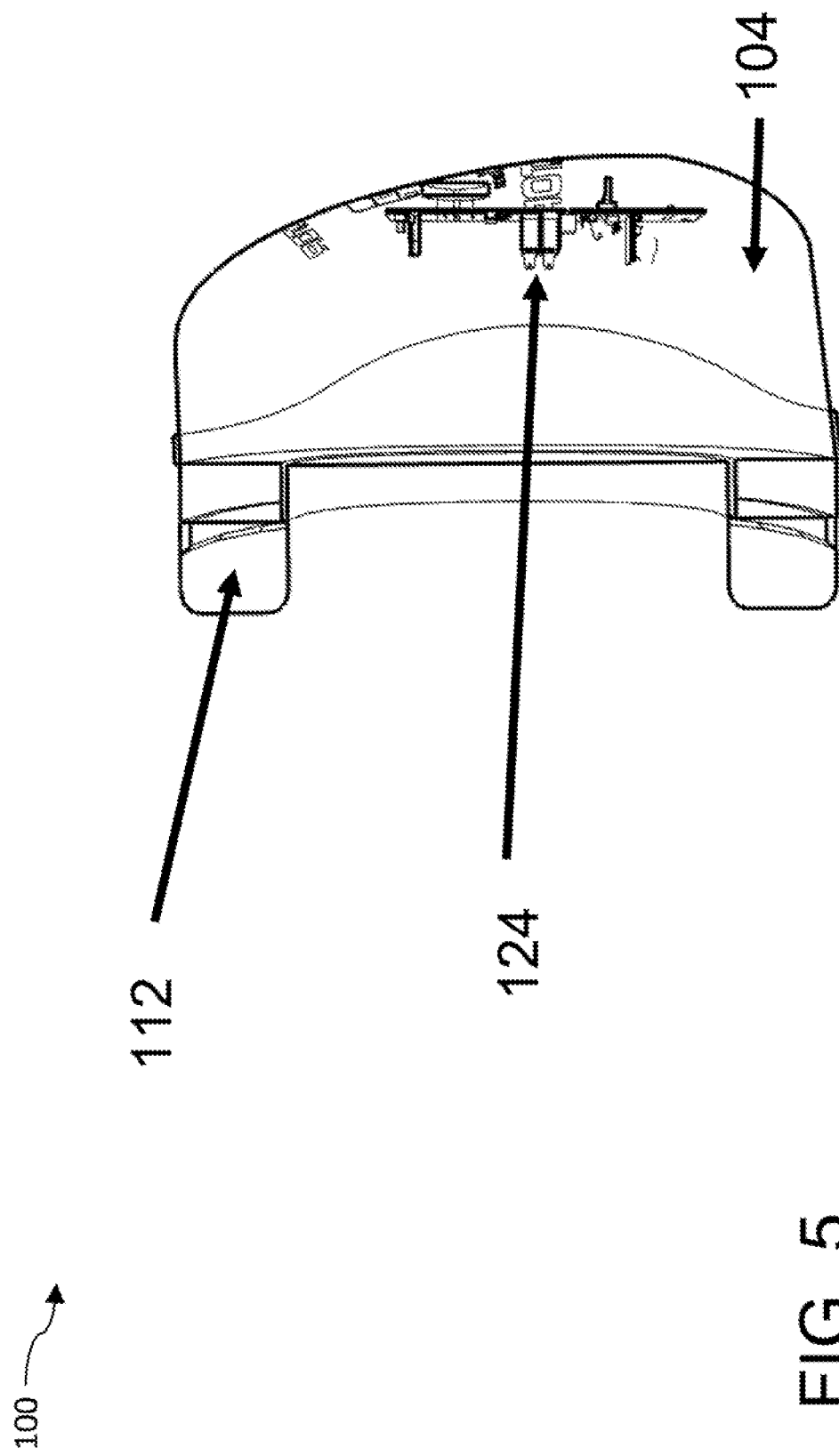
FIG. 5 shows a front sectional view of a device according to an embodiment of the present invention.
Figure 6:
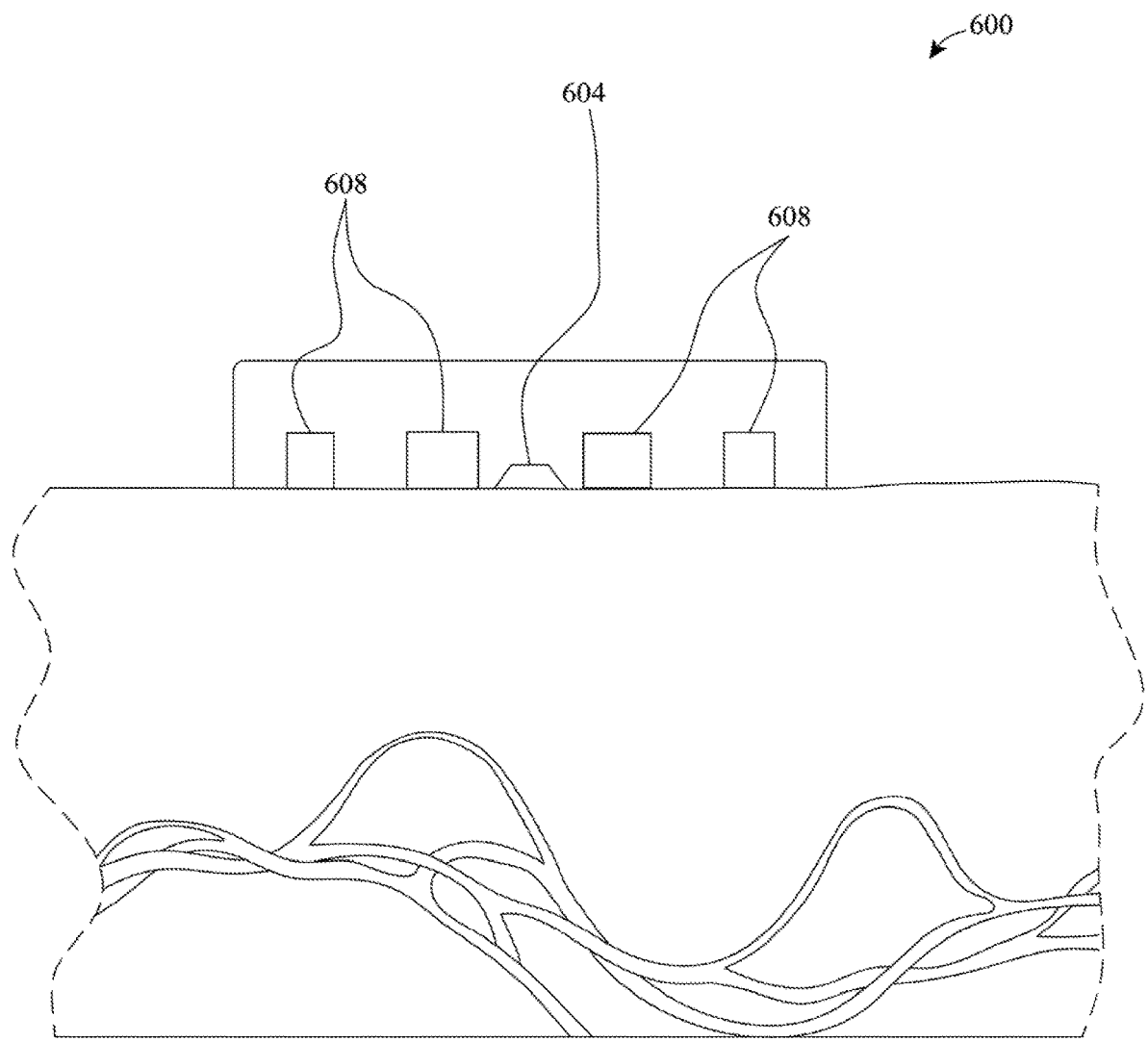
FIG. 6 is a schematic illustration of an exemplary embodiment of a near-infrared spectroscopy sensor.

With continued reference to FIGS. 1-5, alert circuit 120 may be constructed according to any suitable process or combination of processes for constructing an electrical circuit; for instance, and without limitation, alert circuit 120 may include a printed circuit board. Alert circuit 120 may include a battery or other power supply; where alert circuit 120 is integrated in one or more other systems as described in further detail below, alert circuit 120 may draw electrical power from one or more circuit elements and/or power supplies of such systems. Alert circuit 120 may include a memory; memory may include any memory as described below in reference to FIG. 8. Alert circuit 120 may include one or more processors as described in further detail below in reference to FIG. 8, including without limitation a microcontroller or low-power microprocessor. In an embodiment, memory may be used to store one or more signals received from at least a sensor 116. Alert circuit 120 may be communicatively coupled to at least an environmental sensor 124; at least an environmental sensor 124 may be any sensor configured to detect at least an environmental parameter, defined herein as a parameter describing non-physiological data concerning user or surroundings of user, such as acceleration, carbon monoxide, or the like. At least an environmental sensor 124 may include at least a motion sensor, including without limitation one or more accelerometers, gyroscopes, magnetometers, or the like; at least a motion sensor may include an inertial measurement unit (IMU). At least an environmental sensor 124 may include at least a temperature sensor. At least an environmental sensor 124 may include at least an air quality sensor, such as without limitation a carbon monoxide sensor, or other sensor of any gas or particulate matter in air. At least an environmental sensor 124 may include a pressure sensor, for instance to detect air or water pressure external to user. Alert circuit 120 may be attached to housing 104, for instance by incorporation within housing 104; as a non-limiting example and as shown in FIG. 5, the alert circuit 120 may be housed along an inner wall of the housing 104. Alert circuit 120 may be attached to an exterior of housing 104. According to an embodiment, a covering may be placed over housing 104, fully enclosing the alert circuit 120 within the housing 104; the enclosure may include a plastic, a metal, a mesh-type material, and/or any other suitable material. Alert circuit 120 may be in another location not attached to or incorporated in housing 104. Alert circuit 120 may be incorporated into and/or connected to one or more additional elements including any elements incorporating or connected to user signaling devices as described in further detail below. As an alternative to storage of one or more parameter values such as physiological parameters or environmental parameters in memory, alert circuit may transmit the data to one or more remote storage mediums through one or more wired and/or wireless means.

Still viewing FIGS. 1-5, alert circuit 120 may be configured to receive at least a signal from the at least a sensor 116, generate an alarm as a function of the at least a signal, and to transmit the alarm to a user-signaling device 128 communicatively coupled to the alert circuit 120. Alert circuit may periodically sample data from at least a sensor; in a non-limiting example, data may be sampled 75 times per second. In an embodiment, alarm is generated upon detection of any signal at all from at least a sensor 116; for instance, at least a sensor 116 may be configured only to signal alert circuit 120 upon detection of a problematic or otherwise crucial situation. Alternatively or additionally, alert circuit 120 is further configured to detect a physiological alarm condition and generate the alarm as a function of the physiological alarm condition. In an embodiment, a physiological alarm condition includes any physiological condition of user that may endanger user or impair user's ability to perform an important task; as a non-limiting example, if user is flying an aircraft and user's physiological condition is such that user is unable to concentrate, respond rapidly to changing conditions, see or otherwise sense flight controls or conditions, or otherwise successfully operate the aircraft within some desired tolerance of ideal operation, a physiological alarm condition may exist, owing to the possibility of inefficient or dangerous flight that may result. Similarly, if user's physiological condition indicates user is experiencing or about to experience physical harm, is losing or is about to lose consciousness, or the like, a physiological alarm condition may exist.

In an embodiment, and still viewing FIGS. 1-5, detection of a physiological alarm condition may include comparison of at least a physiological parameter to a threshold level. For instance, and without limitation, detection of the physiological alarm condition further comprises determination that the at least a physiological parameter is falling below a threshold level; as an example, blood oxygen levels below a certain cutoff indicate an imminent loss of consciousness, as may blood pressure below a certain threshold. Similarly, alpha wave activity falling below a certain point may indicate entry into early stages of sleep or a hypnogogic state. Comparison to threshold may include comparison of at least a physical parameter to a value stored in memory, which may be a digitally stored value; alternatively or additionally comparison may be performed by analog circuitry, for instance by comparing a voltage level representing at least a physical parameter to a reference voltage representing the threshold, by means of a comparator or the like. Threshold may represent or be represented by a baseline value.

Still referring to FIGS. 1-5, detection of physiological alarm condition may include comparing at least a physiological parameter to at least a baseline value and detecting the physiological alarm condition as a function of the comparison. At least a baseline value may include a number or set of numbers representing normal or optimal function of user, a number or set of numbers representing abnormal or suboptimal function of user, and/or a number or set of numbers indicating one or more physiological parameters demonstrating a physiological alarm condition. At least a baseline value may include at least a threshold as described above. In an embodiment, at least a baseline value may include a typical user value for one or more physiological parameters. For example, and without limitation, at least a baseline value may include a blood oxygen level, blood pressure level, pulse rate, or other circulatory parameter, or range thereof, consistent with normal or alert function in a typical user; at least a baseline value may alternatively or additionally include one or more such values or ranges consistent with loss of consciousness or impending loss of consciousness in a typical user. Similarly, at least a baseline value may include a range of neural oscillations typically associated in users with wakeful or alert states of consciousness, and/or a range of neural oscillations typically associated with sleeping or near-sleeping states, loss of consciousness or the like. Alert circuit 120 may receive a typical user value and using the typical user value as the baseline value; for instance, alert circuit 120 may have typical user value entered into memory of alert circuit 120 by a user, or may receive typical user value over a network or from another device. At least a baseline value may be maintained in any suitable data structure, including a table, database, linked list, hash table, or the like.

Continuing to refer to FIGS. 1-5, typical user value may include a user value matched to one or more demographic facts about user. For instance, a pulse rate associated with loss of consciousness in women may not be associated with loss of consciousness in men, or vice-versa; where user is a woman, the former pulse rate may be used as a baseline value for pulse rate. Baseline value may similarly be selected using a typical value for persons matching user's age, sex, height, weight, degree of physical fitness, physical test scores, ethnicity, diet, or any other suitable parameter. Typical user baseline value may be generated by averaging or otherwise aggregating baseline values calculated per user as described below; for instance, where each user has baseline values established by collection of physiological parameters using devices such as device 100, such values may be collected, sorted according to one or more demographic facts, and aggregated to produce a typical user baseline value to apply to user.

Still referring to FIGS. 1-5, baseline value may be created by collection and analysis of at least a physiological parameter; collection and/or analysis may be performed by alert circuit 120 and/or another device communicatively coupled to alert circuit 120. For instance, receiving a baseline value may include collecting a plurality of samples of the at least a physiological parameter and calculating the baseline value as a function of the plurality of samples. Device 100 may continuously or periodically read or sample signals from at least a sensor 116, recording the results; such results may be timestamped or otherwise co-associated, such that patterns concerning physiological parameters may be preserved, detected, and/or analyzed. For example and without limitation, user pulse rate and/or blood pressure may vary in a consistent manner with blood oxygen level; user blood pressure and/or pulse rate may further vary in a consistent manner with brain wave activity. Additional information from other sensors may similarly collected to form baseline value; for instance, where user is operating a machine, such as an aircraft, data concerning operation, such as flight control data, may be collected and associated with at least a physiological parameter. As a non-limiting example, user's reaction time when operating an aircraft may be measurably slower when user's blood pressure is below a certain amount, while showing no particular change for variations in blood pressure above that amount. Additional information may further be provided by user and/or another person evaluation user behavior and/or performance. For example, during test flights or other operation of an aircraft where user and/or aircraft may be observed, user, a supervisor, or another observer may record information such as the user's performance, the user's feelings or apparent state of health, the performance of the aircraft, and the like. Some factors that may be relatively objectively monitored regarding the overall state of health experience by the user may include how many times the user has to use "anti-G" breathing exercises, or similar activities. In an embodiment, data is received from user and/or observers via numerical ratings, or selections of buttons or other entry devices that map to numerical ratings. Alternatively or additionally, entries may be formed using one or more text entries; text entries may be mapped to numerical ratings or the like using, as a non-limiting example, natural language analysis, textual vector analysis, or the like. Plurality of physiological parameters and/or user entries and other entries may be collected over time, during, for instance a series of routine activities by user.

Continuing to refer to FIGS. 1-5, baseline value may be generated by collection of data from at least an environmental sensor 124. For instance, each set of one or more physiological parameters taken at a particular moment, or over a particular period of time, may be linked in memory to one or more environmental parameters, including without limitation motion-sensor data, air quality data, and the like. This may be used by device 100, as a non-limiting example, to collect relationships between environmental parameters and physiological parameters, such as a relationship between localized or systemic blood pressure, G-forces, and state of consciousness of a user in an aircraft, or a relationship between quality of neural oscillations and external water pressure in a diver. This in turn may be used to produce additional baseline information as described in further detail below.

With continued reference to FIGS. 1-5, plurality of physiological parameters, plurality of environmental parameters, and/or user-entered data may be aggregated, either independently or jointly. For instance, device 100 may calculate an average level, for one or more parameters of at least a physiological parameter, associated with normal or optimal function, health, or performance of user; a standard deviation from the average may also be calculated. This may be used, e.g., to generate an alarm indicating that, for instance, a given physiological parameter has recently shifted more than a threshold amount from its average value. Threshold amount may be determined based on amounts by which a typical user may deviate from average amount before experiencing discomfort, loss of function, or loss of consciousness. Threshold amount may be set as some multiple of standard deviations, as calculated from sensed physiological parameters; for instance, two or more standard deviations from an average value for a given detected physiological parameter may trigger an alarm.

Alternatively or additionally, and still referring to FIGS. 1-5, aggregation may include aggregation of relationships between two or more parameters. For instance, and without limitation, aggregation may calculate a relationship between a first physiological parameter of the at least a physiological parameter and a second physiological parameter of the at least a physiological parameter; this relationship may be calculated, as a non-limiting example, by selecting a first parameter as a parameter associated with a desired state for the user and a second parameter known or suspected to have an effect on the first parameter. For example, first parameter may be blood oxygen level, and second parameter may be blood pressure, such as localized blood pressure in a cranial region; a reduction in cranial blood pressure may be determined to be related to a reduction in cranial blood oxygen level, which in turn may be related to loss of consciousness or other loss of function in user or in a typical user. As another example, aggregation may calculate a relationship between a physiological parameter of the at least a physiological parameter and an environmental parameter. For example, blood oxygen level may be inversely related to an amount of acceleration or G force a user is experiencing in an aircraft; this relationship may be directly calculated from those two values, or indirectly calculated by associating the amount of acceleration or G force with a degree of decrease in cranial blood pressure, which may then be related to blood oxygen levels. Aggregation may calculate a relationship between at least a physiological parameter and user-entered data; for instance, people observing user may note losses of performance or apparent function at times associated with a certain degree of decrease in blood oxygen level or some other physiological parameter. The relationships may be between combinations of parameters: for instance, loss of function may be associated with an increase in G forces coupled with a decrease in pulse rate, or a decrease in blood oxygen coupled with a decrease in alpha waves, or the like.

Still referring to FIGS. 1-5, relationships between two or more of any of physiological parameters, environmental parameters, and/or user-entered parameters may be determined by one or more machine-learning algorithms. Machine-learning algorithms as used herein are processes executed by computing devices to improve accuracy and efficiency of other processes performed by the computing devices, or detect relationships between data sets, through statistical or mathematical measures of accuracy and efficiency. Machine learning may function by measuring a difference between predicted answers or outputs and goal answers or outputs representing ideal or "real-world" outcomes the other processes are intended to approximate. Predicted answers or outputs may be produced by an initial or intermediate version of the process to be generated, which process may be modified as a result of the difference between predicted answers or outputs and goal answers or outputs. Initial processes to be improved may be created by a programmer or user, or may be generated according to a given machine-learning algorithm using data initially available. Inputs and goal outputs may be provided in two data sets from which the machine learning algorithm may derive the above-described calculations; for instance a first set of inputs and corresponding goal outputs may be provided, and used to create a mathematical relationship between inputs and outputs that forms a basis of an initial or intermediate process, and which may be tested against further provided inputs and goal outputs. Data sets representing inputs and corresponding goal outputs may be continuously updated with additional data; machine-learning process may continue to learn from additional data produced when machine learning process analyzes outputs of "live" processes produced by machine-learning processes. As a non-limiting example, an unsupervised machine-learning algorithm may be performed on training sets describing co-occurrences of any or all parameters in time; unsupervised machine-learning algorithm may calculate relationships between parameters and such co-occurrences. This may produce an ability to predict a likely change in a physiological parameter as a function of detected changes in one or more environmental parameters; thus, a physiological alarm condition may be detected when a set of alarm parameters are trending in a way associated with decreases in blood oxygen, causing a blood oxygen warning to be generated before any decrease in blood oxygen is detected.

With continued reference to FIGS. 1-5, a supervised machine learning algorithm may be used to determine an association between one or more detected parameters and one or more physiological alarm conditions or other outcomes or situations of interest or concern. For instance, a supervised machine-learning algorithm may be used to determine a relationship between one or more sets of parameters, such as physiological parameters, environmental parameters, and/or user-entered information, and one or more physiological alarm conditions. To illustrate, a mathematical relationship between a set of physiological and environmental parameters as described above and a loss of consciousness, or near loss of consciousness, by user, may be detected by a supervised machine-learning process; such a process may include a linear regression process, for instance, where a linear combination of parameters may is assumed to be associated with a physiological alarm condition, and collected parameter data and associated data describing the physiological alarm condition are evaluated to determine the linear combination by minimizing an error function relating outcomes of the linear combination and the real-world data. Polynomial regression may alternatively assume one or more polynomial functions of parameters and perform a similar minimization process. Alternatively or additionally neural net-based algorithms or the like may be used to determine the relationship.

Still viewing FIGS. 1-5, each of the above processes for aggregation and/or machine learning may further be compared to test data, such as data gathered concerning user physiological parameters, performance, and/or function, in one or more testing facilities or protocols; such facilities or protocols may include, for instance, centrifuge testing of a user's response to acceleration and/or G forces, tests administered to monitor one or more physiological parameters and/or user function or performance under various adverse conditions such as sleep deprivation, boredom, and the like, or any other tests administered to determine the effect of various conditions on user. Such test data may be collected using device 100, or alternatively may be collected using one or more other devices, medical facilities, and the like. Any aggregation and/or machine learning as described above may be applied to test data, independently or combined with other data gathered as described above; for instance, in an embodiment, test data may be combined with typical user data to achieve a first baseline, which may be compared to further data gathered as described above to modify the baseline and generate a second baseline using any suitable aggregation or machine-learning methodology. Collected and/or aggregated data may be provided to users, such as supervisors or commanders, who may use collected and/or aggregated data to monitor state of health of individual users or groups of users.

With continued reference to FIGS. 1-5, in an illustrative example, detection of a physiological alarm condition may include determination, by the alert circuit 120, that the user is losing consciousness. Alternatively or additionally, detection may include determination that user is about to lose consciousness. This may be achieved by comparing one or more physiological parameters and/or environmental parameters to a relationship, threshold, or baseline, which may be any relationship, threshold, or baseline as described above; for instance and without limitation, where blood oxygen level drops below a threshold percentage of a baseline level, below an absolute threshold amount, below a certain number of standard deviations, or the like, alert circuit 120 may determine that user is about to lose consciousness or is losing consciousness, and issue an alarm. Alternatively or additionally, aggregation as described above may determine that imminent loss of consciousness is predicted by a particular set of values for one or more parameters as described above, alert circuit 120 may detect a physiological alarm condition by detecting the particular set of values, indicating that user is about to lose consciousness. In an embodiment, determination of user state and/or physiological alarm condition may filter out anomalous or transient readings, or readings altered by motion of one or more elements of user's body or environment; for instance, determination may include determination of a particular parameter value for longer than a predetermined amount of time.

As another example, and still viewing FIGS. 1-5, detection of the physiological alarm condition further comprises determination that the user is falling asleep; this may occur, for instance, where a neural activity sensor detects that a user is entering into an early stage of sleep, or "dozing off," for instance by detection of a change in brainwaves. In an embodiment, alert circuit 120 may generate an alarm where alpha wave activity drops by a threshold percentage, by a threshold amount, or the like; alternatively or additionally, one or more sets of brainwave patterns determined by alert circuit 120 to be associated with user falling asleep, for instance by aggregation or machine-learning methods as described above, may be detected by alert circuit 120 via at least a neural activity sensor, triggering an alarm. This may, as a non-limiting example, aid in preventing a commercial pilot who is not actively operating flight controls from partially or wholly falling asleep, which is a particular concern on long flights.

With continued reference to FIGS. 1-5, detection of a physiological alarm condition may further include detection of at least an environmental parameter, and detection of physiological alarm condition as a function of the at least an environmental parameter. For instance, aggregation and/or machine learning processes as described above may determine that a reduction in cranial blood pressure coupled with an increase in acceleration indicates a probable loss of consciousness in a user; an alarm may therefore be triggered by detection, by alert circuit 120, of that combination of decreased cranial blood pressure and increased acceleration.

Still viewing FIGS. 1-5, alert circuit 120 may be communicatively coupled to at least a user-signaling device 128. In an embodiment, at least a user-signaling device 128 may be incorporated in device 100; for instance, at least a user-signaling device 128 may be attached to or incorporated in housing 104. Where at least a user-signaling device 128 contacts an exterior body surface of user, housing 104 may act to place at least a user-signaling device 128 in contact exterior body surface of user. Alternatively or additionally, device 100 may communicate with a user-signaling device 128 that is not incorporated in device 100, such as a display, headset, or other device provided by a third party or the like, which may be communicatively coupled to alert circuit 120.

Continuing to refer to FIGS. 1-5, at least a user-signaling device 128 may include any device capable of transmitting an audible, tactile or visual signal to a user when triggered to do so by alert circuit 120. In an embodiment, and as a non-limiting example, at least a user-signaling device 128 may include a bone-conducting transducer in vibrational contact with a bone beneath the exterior body surface. A bone-conducting transducer, as used herein, is a device or component that converts an electric signal to a vibrational signal that travels through bone placed in contact with the device or component to an inner ear of user, which interprets the vibration as an audible signal. Bone-conducting transducer may include, for instance, a piezoelectric element, which may be similar to the piezoelectric element found in speakers or headphones, which converts an electric signal into vibrations. In an embodiment, bone-conducting transducer may be mounted to housing 104 in a position placing it in contact with a user's bone; for instance, where housing 104 includes or is incorporated in an ear cup, housing 104 may place bone-conducting transducer in contact with user's skull just behind the ear, over the sternocleidomastoid muscle. Likewise, where housing 104 includes a headset, mask, or helmet, housing 104 may place bone-conducting transducer in contact with a portion of user's skull that is adjacent to or covered by headset, mask, or helmet.

Still referring to FIGS. 1-5, at least a user-signaling device 128 may further include an audio output device. Audio output device may include any device that converts an electrical signal into an audible signal, including without limitation speakers, headsets, headphones, or the like. As a non-limiting example, audio output device may include a headset speaker of a headset incorporating or connected to device 100, a speaker in a vehicle user is traveling in, or the like. At least a user-signaling device 128 may include a light output device, which may be any device that converts an electrical signal into visible light; light output device may include one or more light source 604s such as LEDs, as well as a display, which may be any display as described below in reference to FIG. 8. At least a user-signaling device 128 may include a vehicular display; at least a vehicular display may be any display or combination of displays presenting information to a user of a vehicle user is operating. For instance, at least a vehicular display may include any combination of audio output devices, light output devices, display screens, and the like in an aircraft flight console, a car dashboard, a boat dashboard or console, or the like; alert circuit 120 may be communicatively coupled to vehicular display using any form of communicative coupling described above, including without limitation wired or wireless connection. At least a user-signaling device 128 may include a helmet display; helmet display may include any visual, audio, or tactile display incorporated in any kind of helmet or headgear, which may be communicatively coupled to alert circuit 120 according to any form of communicative coupling as described above.

Still viewing FIGS. 1-5, user signaling device and/or alert circuit 120 may be programmed to produce a variety of indications, which may correspond to various physiological alarm conditions and/or contexts. Possible indications may be, but are not limited to: imminent unconsciousness, substandard oxygenation, erratic pulse, optimum oxygenation, and/or any other suitable indication, while maintaining the spirit of the present invention. Each such indication may have a distinct pattern of audible, visual, and/or textual indications; each indication may include, for instance, an audible or textual warning or description of a physiological alarm condition. Any of the above user-signaling devices 128 and/or signals may be used singly or in combination; for instance, a signal to user may include an audio signal produced using a bone-conducting transducer, a verbal warning message output by an audio output device, and a visual display of an image or text indicating the physiological alarm condition. Persons skilled in the art, upon reviewing the entirety of this disclosure, will be aware of various combinations of signaling means and/or processes that may be employed to convey a signal to user. In an embodiment, in addition to transmitting an alarm to user signaling device, alert circuit may transmit a signal to one or more automated vehicular controls or other systems to alleviate one or more environmental parameters contributing to physiological alarm condition. For instance, and without limitation, an automated aircraft control may receive an indication of hypoxia while a motion sensor indicates high acceleration; aircraft control may reduce acceleration to alleviate the hypoxia. Persons skilled in the art, upon reviewing the entirety of this disclosure, may be aware of various additional ways in which automated systems may act to alleviate a physiological alarm condition as described herein.

Figure 7:
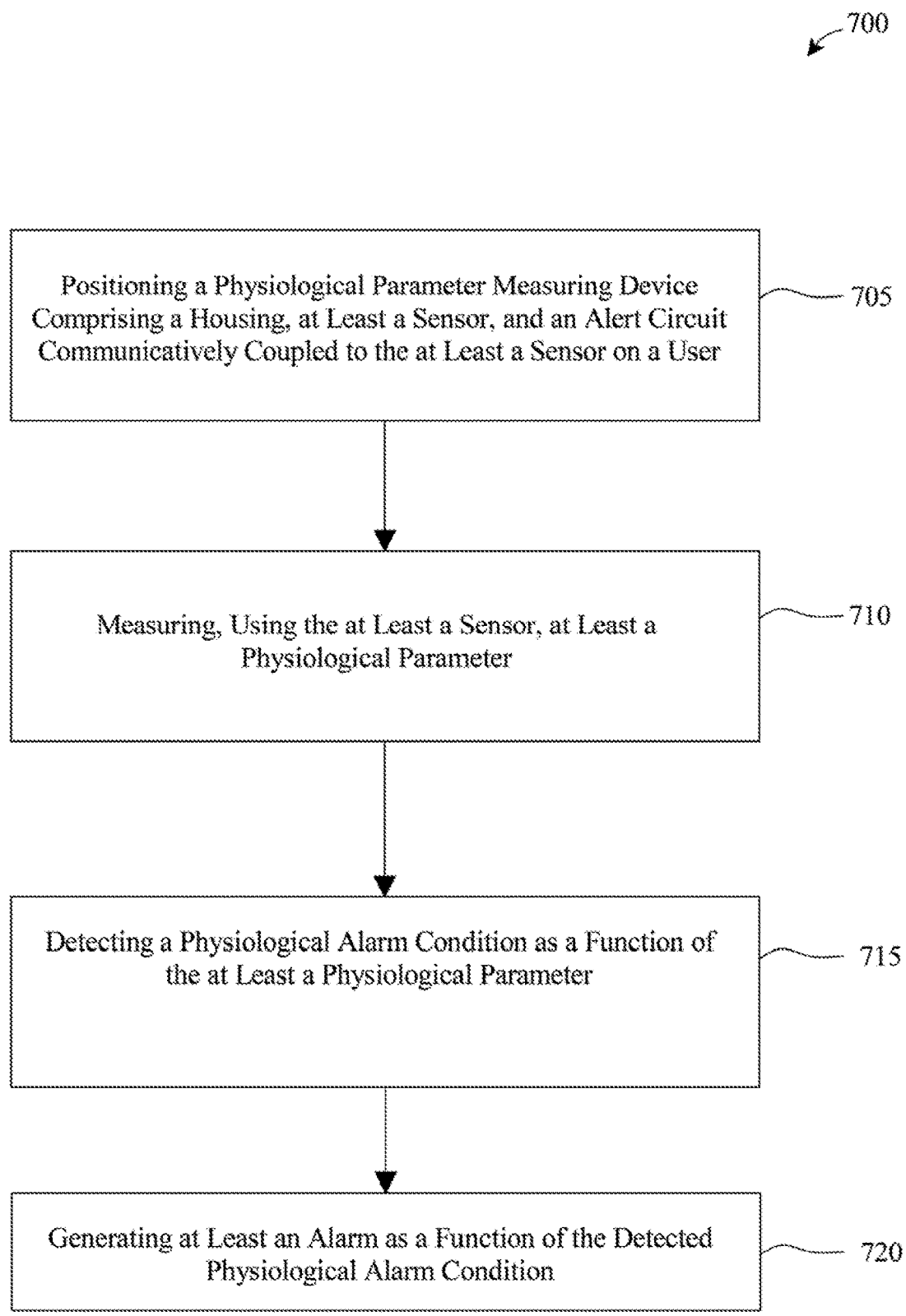
FIG. 7 shows a flowchart of a method of using the human performance oxygen sensor according to an embodiment of the present invention.

Referring now to FIG. 7, an exemplary embodiment of a method 700 of measuring physiological parameters 100 is illustratively depicted. At step 705, a physiological parameter measuring device comprising a housing 104, at least a sensor 116, and an alert circuit 120 communicatively coupled to the at least a sensor 116 is positioned on a user. This may be performed, for instance, as described above in reference to FIGS. 1-5. Positioning may include mounting housing 104 on an exterior body surface of the user. Positioning may include placing at least a sensor 116 in contact with exterior body surface. As a non-limiting example, at least a sensor 116 may rest behind the ear on the neck of the user, over the sternocleidomastoid muscle.

At step 710, with continued reference to FIG. 7, alert circuit 120 measures at least a physiological parameter using at least a sensor 116. In an embodiment, this may be performed as described above in reference to FIGS. 1-5. For instance, where sensor includes at least a NIRS 600 sensor, sensor may measure one or more signals from the user pertaining to the oxygenation of the user. The signals may include, but are not limited to, pulse oximetry, pulse, temperature, and/or any other relevant measurement. NIRS 600 sensor may emit near-infrared (red) light into soft tissue and measure how much of the near-infrared light is absorbed by said tissue and how much is reflected. According to an embodiment, the sensing components of the NIRS 600 sensor may act essentially as specialized photoresistors. Their resistivity may change as a function of the intensity of light reflected from the tissue. Since well-oxygenated blood (defined as oxygen-bound hemoglobin) absorbs more red light than poorly oxygenated blood, a correlation between the resistivity of the sensor and the blood oxygenation may be ascertained as a function of the resistivity.

Still viewing FIG. 7, at step 715, a physiological alarm condition is detected by alert circuit 120 as a function of the at least a physiological parameter. This may be implemented, for instance, as described above in reference to FIGS. 1-5. For example, and without limitation, alert circuit 120 may predicts whether a user is going to experience an impending lack of consciousness. According to an embodiment, alert circuit 120 may constantly monitor blood oxygenation by virtue of a NIRS sensor. According to an embodiment, when oxygenation drops by a predefined percentage, the alert circuit 120 may predict that the user is going to experience an impending lack of consciousness. Any other combination of physiological and/or environmental parameters may be used to detect physiological alarm condition, as described above in reference to FIGS. 1-5.

With continued reference to FIG. 7, at step 720, alert circuit 120 generates at least an alarm as a function of the detected physiological alarm condition. This may be performed as described above in reference to FIGS. 1-5. Alert circuit 120 may signal user as a function of detected physiological alarm condition; this may be implemented as described above in reference to FIGS. 1-5. For instance, and without limitation, where alert circuit 120 predicts that the user is going to experience an impending lack of consciousness, the alert circuit 120 may sends a signal to bone conduction transducer, generating a user signal. Similarly, and as described above, alert circuit 120 may further send a signal to a third-party device, either wirelessly or through a wired connection, alerting a third party of any relevant predictions made by the alert circuit 120 while the device for measuring physiological parameters 100 is being used.

Device for measuring physiological parameters 100 may be used is various fields, according to various embodiments of the present invention. According to an embodiment, the device for measuring physiological parameters 100 may be used in conjunction with military aviation. For example, the human performance oxygen sensor may be used for military aviation uses that rely on stored oxygen, e.g., for use in fighter jets and high altitude parachuting. During operation of fighter jets and while performing high altitude parachuting, there is a risk of hypoxia and the inherent need to wear a helmet. The device for measuring physiological parameters 100 may be incorporated into such helmets, thus measuring the wearer's vital oxygenation signals while the wearer is wearing the helmet.

According to various embodiments, device for measuring physiological parameters 100 may be used in conjunction with commercial aviation headsets, firefighting uses, and/or in any other suitable field where the measurement of human oxygenation is relevant or necessary for the safety of individuals or for any other relevant reason. According to various embodiments, iterative additional developments of the product include incorporation of a carbon dioxide sensor, reduction in size/weight, removal of the battery to utilize host system available power from the aircraft or vehicle, and/or the inclusion or exclusion of various other suitable components while maintaining the spirit of the present principles. In testing performed using a reduced oxygen breathing device (ROBD) to simulate atmospheric conditions at various altitudes, in which device 100 was compared to a conventional finger-mounted oxygen sensor, it was found that embodiments of device 100 were able to detect decreased blood oxygen levels up to 15 seconds earlier than previously available systems, resulting in a substantially improved opportunity for users to correct conditions leading to hypoxia; this in turn allowed users to avert symptoms of hypoxia in some cases, and generally to reduce the length and severity of symptoms, both of which are crucial for improving outcomes during flight. Alarms were triggered by device 100 just as users were reporting initial sensation of symptoms. Subsequent testing on flight sorties confirmed high degrees of reliability in detection of physiological alarm conditions.

According to various embodiments, device 100 may further include incorporation of a pulse oximetry sensor and a carbon dioxide sensor to incorporate the existing product into a fire helmet. The power source and signal may be transmitted to an existing or newly developed two-way radio system in order to allow a fire chief to receive real-time data on all the members of his firefighting force. By transmitting and receiving this data, the fire chief is able to receive real time location and performance data of every single member of his time, optimizing the team's performance.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
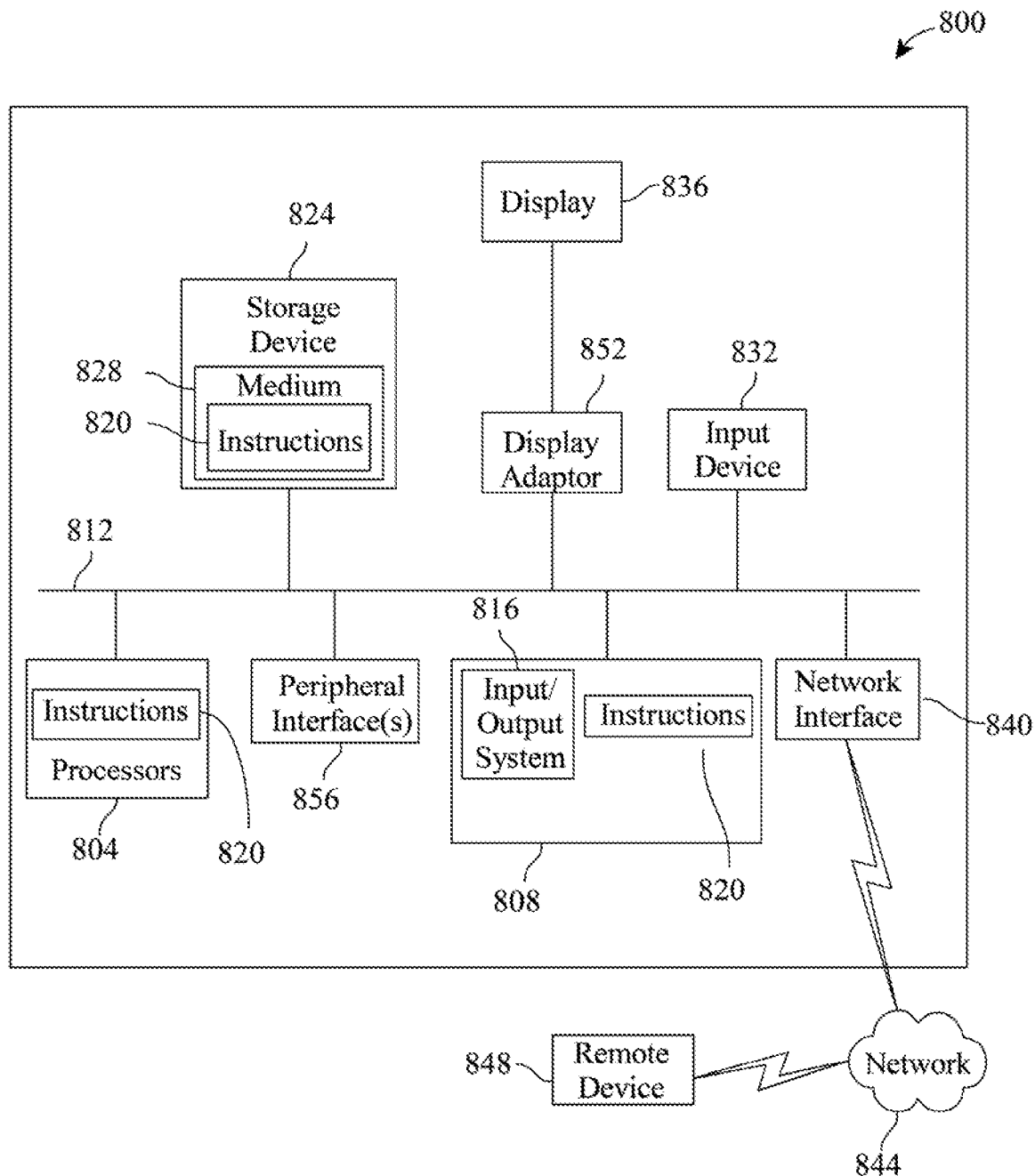
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system, such as the device 100 disclosed above, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Memory 808 may include various components (e.g., machine-readable media) including, but not limited to, a random access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, devices and/or software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for measuring physiological parameters, the system comprising:
    a housing configured to be mounted to an exterior body surface of a user, wherein the housing comprises at least an earcup;
    at least a physiological sensor attached to the housing and configured to contact the exterior body surface at a locus on a head of the user, the at least a sensor configured to detect at least a first physiological parameter identifying a first neural activity of the user and at least a second physiological parameter identifying a second neural activity of the user and transmit an electrical signal as a result of the detection;
    at least an environmental sensor;
    a first physiological condition baseline value associated with a first predetermined environmental parameter detectable by the environmental sensor;
    a second physiological condition baseline value associated with a second predetermined environmental parameter detectable by the environmental sensor; and
    an alert circuit communicatively coupled to the at least sensor the alert circuit configured to:
        receive at least a signal from the at least a physiological sensor;
        detect an environmental parameter using the at least an environmental sensor;
        detect a physiological alarm condition, wherein detecting the physiological alarm condition further comprises:
            comparing the first neural activity of the user and the second neural activity of the user to at least one of the first or second physiological condition baseline values according to a detected environmental parameter to determine a function of the user; and
            determining based on the comparison a diminishment in the function of the user;
        generate an alarm based on the physiological alarm condition; and
        transmit the alarm to a user-signaling device communicatively coupled to the alert circuit.

2. The system of claim 1, wherein the housing further comprises an outer shell.

3. The system of claim 1, wherein the housing is configured to be inserted between a helmet worn on a head of the user and the exterior body surface.

4. The system of claim 1, wherein the housing further comprises a mask.

5. The system of claim 1, further comprising a substantially pliable seal attached to the housing and configured to be disposed against the exterior body surface.

6. The system of claim 1, wherein the at least a sensor is configured to contact a locus on the exterior body surface where substantially no muscle is located between the exterior body surface and an underlying bone structure.

7. The system of claim 1, wherein the at least a physiological parameter further comprises at least a circulatory parameter.

8. The system of claim 7, wherein the at least a circulatory parameter further comprises a blood oxygen level.

9. The system of claim 7, wherein the at least a circulatory parameter includes a pulse rate.

10. The system of claim 7, wherein the at least a circulatory parameter includes a blood pressure.

11. The system of claim 1, wherein the at least a sensor is configured to detect a plethysmograph of at least a bodily fluid of the user.

12. The system of claim 1, wherein the at least a sensor further comprises a near-infrared spectroscopy sensor.

13. The system of claim 1, wherein the at least a sensor includes a neural activity sensor.

14. The system of claim 13, wherein the neural activity sensor further comprises an electroencephalographic sensor.

15. The system of claim 13, wherein the neural activity sensor further comprises a magnetoencephalographic sensor.

16. The system of claim 1, wherein configuration of the alert circuit to detect the physiological alarm condition further comprises configuration to determine that the user is falling asleep.

17. The system of claim 1, wherein configuration of the alert circuit to detect further comprises configuration to receive a typical user value and use the typical user value as the first physiological condition baseline value.

18. The system of claim 1 wherein configuration of the alert circuit to detect further comprises configuration to:
collect a plurality of samples from the at least a physiological sensor; and
calculate the first physiological condition baseline value based on the plurality of samples.

19. The system of claim 1, wherein the at least a user-signaling device further comprises a bone-conducting transducer configured to be in vibrational contact with a bone beneath the exterior body surface.

20. The system of claim 1, wherein the at least a user-signaling device further comprises an audio output device.

21. The system of claim 1, wherein the at least a user-signaling device further comprises a light output device.

22. The system of claim 1, wherein the at least a user-signaling device further comprises a vehicular display.

23. The system of claim 1, wherein the at least a user-signaling device further comprises a helmet display.

24. The system of claim 1, wherein the alert circuit is further configured to generate the mathematical relationship between the set of physiological and environmental parameters and loss of consciousness using a supervised machine-learning algorithm.

25. The system of claim 1, wherein the at least a physiological sensor comprises a first sensor and a second sensor distinct from the first sensor.

26. The system of claim 1, further comprising a second physiological sensor, said second physiological sensor configured to detect a third physiological parameter identifying a third neural activity of the user and a fourth physiological parameter identifying a fourth neural activity of the user, wherein the third and fourth neural activities of the user are of a type of neural activity distinct from a type of neural activity of the first and second neural activities.

27. The sensor of claim 26, wherein detecting the physiological alarm condition further comprises:
comparing the third neural activity and the fourth neural activity of the user to at least one of the first or second physiological condition baselines according to the detected environmental parameter; and
wherein determining a diminishment in the function of the user is further based upon the comparison of the third neural activity and the fourth neural activity of the user to at least one of the first or second physiological condition baselines.

28. A method of measuring at least a physiological parameter, the method comprising:
positioning a physiological parameter measuring device comprising a housing configured to be mounted to an exterior body surface of a user, at least a sensor attached to the housing and configured to contact an exterior body surface of the user, and an alert circuit communicatively coupled to the at least a sensor on the user, wherein positioning further comprises:
mounting the housing on an exterior body surface of the user; and
placing the at least a sensor in contact with the exterior body surface;
measuring, by the alert circuit and using the at least a sensor, at least a first physiological parameter identifying a first neural activity of the user and at least a second physiological parameter identifying a second neural activity of the user;
generating a first physiological condition baseline value associated with a first predetermined environmental parameter detectable by an environmental sensor, and a second physiological condition baseline value associated with a second predetermined environmental parameter detectable by the environmental sensor;
detecting, by the alert circuit, a physiological alarm condition, based on the at least a physiological parameter wherein detecting the physiological alarm condition further comprises:
comparing the first neural activity of the user and the second neural activity of the user to at least one of the first or second physiological condition baselines according to a detected environmental parameter; and
determining based on the comparison that a diminishment in the function of the user;
generating, by the alert circuit, at least an alarm as based on the detected physiological alarm condition.

29. The method of claim 28, wherein detecting the physiological alarm condition further comprises generating the mathematical relationship between the set of physiological and environmental parameters and loss of consciousness using a supervised machine-learning algorithm.

* * * * *